United States Patent [19]
Berg

[11] Patent Number: 5,421,965
[45] Date of Patent: Jun. 6, 1995

[54] SEPARATION OF GLYCERINE FROM BIS(HYDROXYMETHYL)TETRAHYDROFURAN BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 283,641

[22] Filed: Aug. 1, 1994

[51] Int. Cl.⁶ .................. B01D 3/36; C07C 31/22; C07D 307/06
[52] U.S. Cl. .......................... 203/58; 203/60; 203/68; 203/69; 203/70; 547/502; 568/869
[58] Field of Search .............. 203/68, 69, 70, 60, 203/52, 58; 568/869; 549/502

[56] References Cited
U.S. PATENT DOCUMENTS

| | | | |
|---|---|---|---|
| 2,993,912 | 7/1961 | Dunlop | 549/502 |
| 3,040,062 | 6/1962 | Hales | 549/502 |
| 4,655,879 | 4/1987 | Brockmann et al. | 568/869 |
| 4,975,158 | 12/1990 | Berg | 203/68 |
| 4,980,033 | 12/1990 | Berg | 203/68 |
| 5,190,622 | 3/1993 | Berg | 203/69 |
| 5,198,077 | 3/1993 | Berg | 203/60 |

Primary Examiner—Wilbur Bascomb, Jr.

[57] ABSTRACT

Glycerine is difficult to separate from bis(hydroxymethyl)tetrahydrofuran by conventional distillation or rectification because of the proximity of their boiling points. Glycerine can be readily separated from bis(hydroxymethyl)tetrahydrofuran by azeotropic distillation. Effective agents are m-xylene, beta-pinene and dicyclopentadiene.

2 Claims, No Drawings

SEPARATION OF GLYCERINE FROM BIS(HYDROXYMETHYL)TETRAHYDROFURAN BY AZEOTROPIC DISTILLATION

FIELD OF THE INVENTION

This invention relates to a method for separating glycerine from bis(hydroxymethyl)tetrahydrofuran (BHMTHF) using certain organic liquids as the agent in azeotropic distillation.

DESCRIPTION OF PRIOR ART

Azeotropic distillation is the method of separating close boiling compounds or azotropes from each other by carrying out the distillation in a multiplate rectification column in the presence of an added liquid, said liquid forming an azeotrope with one orb orb of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating theazeotrope former from the more volatile component are cooling and phase separation or solvent extraction.

The usual method of evaluating theeffectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, Both Products (Mole Fraction) | Relative Volatility | | | | | | |
|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

There are a number of commercial processes which produce a complex mixture of glycerine, B.P.=290° C. and glycols. One of the glycols often present is bis(hydroxymethyl)tetrahydrofuran, B.P.=265° C. The relative volatility between these two is 1.09 which makes it very difficult to separate them by conventional rectification. Azeotropic distillation would be an attractive method of effecting the separation of glycerine from bis(hydroxymethyl)tetrahydrofuran (BHMTHF) if agents can be found that (1) will create a large apparent relative volatility between glycerine and BHMTHF and (2) are easy to recover from glycerine. Table 2 shows the relative volatility required to obtain 99% purity. With no agent, the relative volatility is 1.09 and 144 actual plates are required. With an agent giving a relative volatility of 2.0, only 19 actual plates are required.

TABLE 2

Theoretical and Actual Plates Required vs. Relative Volatility for Glycerine-BHMTHF Separation

| Relative Volatility | Theoretical Plates Required At Total Reflux, 99% Purity | Actual Plates Required 75% Efficiency |
|---|---|---|
| 1.0$^9$ | 108 | 14$^4$ |
| 1.7 | 18 | 24 |
| 2.0 | 14 | 19 |

OBJECTIVE OF THE INVENTION

The object of this invention is to provide a process or method of azeotropic distillation that will enhance the relative volatility of glycerine from BHMTHF in their separation in a rectification column. It is a further object of this invention to identify organic compounds which in addition to the above constraints, are stable, can be separated from glycerine and recycled to the azeotrope column with little decomposition.

SUMMARY OF THE INVENTION

The objects of this invention are to provide a process for separating glycerine from bis(hydroxymethyl)tetrahydrofuran which entails the use of certain organic compounds as the agent in azeotropic distillation.

DETAILED DESCRIPTION OF THE INVENTION

I have discovered that certain organic compounds will greatly improve the relative volatility of glycerinelto bis(hydroxymethyl)tetrahydrofuran and permit the separation of glycerine from BHMTHF by rectification when employed as the agent in azeotropic distillation. Table 3 lists the compounds that I have found to be effective. They are benzyl benzoate, ethyl salicylate, 3-carene, ethyl benzene, o-xylene, m-xylene, p-xylene, diisopropyl benzene, 2,3,4-trimethyl pentane, terpinolene, limonene, pyridine, carane, p-mentha-1,5-diene, alpha-terpinene, decane, dodecane, decalin, tetralin, cyclohexane, 1-octene, heptane, hexane, isobutyl acetate, beta-pinene and dicyclopentadiene.

TABLE 3

Effective Azeotropic Distillation Agents For Separating Glycerine From bis(Hydroxymethyl) tetrahydrofuran (BHMTHF)

| Compounds | Relative Volatility |
|---|---|
| None | 1.09 |
| Benzyl benzoate | 2.0 |
| Ethyl salicylate | 1.8 |
| 3-Carene | 1.6 |
| Ethyl benzene | 2.0 |
| o-Xylene | 1.9 |
| m-Xylene | 1.71** |
| p-Xylene | 1.2 |
| Diisopropyl benzene | 2.0* |
| 2,3,4-Trimethyl pentane | 2.0* |
| Terpinolene | 2.0 |
| Limonene | 2.0 |
| Pyridine | 2.0* |
| Carane | 2.0 |
| p-Mentha-1,5-diene | 2.0 |
| alpha-Terpinene | 2.0 |
| Decane | 2.0 |
| Dodecane | 2.0*** |
| Decalin | 2.0· |
| Tetralin | 1.5 |
| Cyclohexane | 1.8 |
| 1-Octene | 2.0 |
| Heptane | 2.0* |
| Hexane | 2.0* |
| Isobutyl acetate | 1.3* |
| beta-Pinene | 1.7** |

TABLE 3-continued
Effective Azeotropic Distillation Agents For Separating
Glycerine From bis(Hydroxymethyl) tetrahydrofuran (BHMTHF)

| Compounds | Relative Volatility |
| --- | --- |
| Dicyclopentadiene | 1.6 |

*Very little glycerine in the azeotrope
**Data from rectification column
***Brings BHMTHF out as overhead product

THE USEFULNESS OF THE INVENTION

The usefulness or utility of this invention can be demonstrated by referring to the data presented in Tables 2 and 3. All of the successful agents show that glycerine can be separated from BHMTHF by means of azeotropic distillation in a rectification column and that the ease of separation as measured by relative volatility is considerable.

WORKING EXAMPLES

Example 1

Thirty-two grams of glycerine, 8 grams of BHMTHF and 40 grams of dicyclopentadiene were charged to a vapor-liquid equilibrium still and refluxed for four hours. Analysis indicated a vapor composition of 84.1% glycerine, 15.9% BHMTHF; a liquid composition of 76.2% glycerine, 23.8% BHMTHF. This is a relative volatility of 1.65.

Example 2

Seventy-five grams of glycerine, 25 grams of BHMTHF and 140 grams of m-xylene were placed in the stillpot of a 5.6 theoretical plate glass perforated plate rectification column and refluxed for nine hours. The overhead composition was 97.6% glycerine, 2.4% BHMTHF; the bottoms composition was 66.9% glycerine, 33.1 % BHMTHF. This is a relative volatility of 1.71.

Example 3

Seventy-five grams of glycerine, 25 grams of BHMTHF and 140 grams of beta-pinene were placed in the stillpot of a 5.6 theoretical plate glass perforated plate rectification column refluxed for nine hours. The overhead composition was 95.2% glycerine, 4.8% BHMTHF; the bottoms composition was 50.2% glycerine, 49.8% BHMTHF. This is a relative volatility of 1.7.

Example 4

Thirty-two grams of glycerine, 8 grams of BHMTHF and 40 grams of dodecane were charged to a vapor-liquid equilibrium still and refluxed for four hours. Analysis indicated a vapor composition of 39.1% glycerine, 60.9% BHMTHF; a liquid comoosition of 63.7% glycerine, 36.3% BHMTHF. This is a relative volatility of BHMTHF to glycerine of 2.7.

I claim:

1. A method for recovering glycerine from bis (hydroxymethyl) tetrahydrofuran which comprises distilling a mixture of glycerine and bis(hydroxymethyl)tetrahydrofuran in the presence of an azeotrope forming agent, recovering the glycerine and the azeotrope forming agent as overhead product and obtaining the bis(hydroxymethyl)tetrahydrofuran as bottoms product, wherein said azeotrope forming agent consists of one material selected from the group consisting of benzyl benzoate, ethyl salicylate, 3-carene, ethyl benzene, o-xylene, m-xylene, p-xylene, diisopropyl benzene, 2,3,4-trimethylpentane, terpinolene, limonene, pyridine, carane, p-mentha-1,5-diene, alpha -terpinene, decane, decalin, tetralin, cyclohexane, 1-octene, heptane, hexane, isobutyl acetate, beta-pinene and dicyclopentadiene.

2. A method for recovering bis(hydroxymethyl)tetrahydrofuran from glycerine which comprises distilling a mixture of bis(hydroxymethyl)tetrahydrofuran and glycerine in the presence of an azeotrope forming agent, recovering the bis(hydroxymethyl)tetrahydrofuran and the azeotrope forming agent as overhead product and obtaining the glycerine as bottoms product, wherein said azeotrope forming agent is dodecane.

* * * * *